United States Patent [19]

Parry et al.

[11] Patent Number: 4,927,839

[45] Date of Patent: May 22, 1990

[54] METHOD OF PREVENTING FUNGAL ATTACK ON WOOD, HIDES, LEATHER OR PAINT FILMS USING A TRIAZOLE

[75] Inventors: Keith P. Parry; Paul A. Worthington, both of Maidenhead; William G. Rathmell, Wokingham, all of England

[73] Assignee: Imperial Chemical Industries PLC, London, England

[21] Appl. No.: 854,819

[22] Filed: Apr. 23, 1986

Related U.S. Application Data

[60] Continuation of Ser. No. 579,012, Feb. 10, 1984, Pat. No. 4,595,406, which is a division of Ser. No. 183,410, Sep. 3, 1980, Pat. No. 4,551,469, which is a continuation-in-part of Ser. No. 124,253, Feb. 25, 1980, Pat. No. 4,654,332.

[30] Foreign Application Priority Data

Mar. 7, 1979 [GB] United Kingdom ............... 7908003
Sep. 21, 1979 [GB] United Kingdom ............... 7932819
Feb. 15, 1980 [GB] United Kingdom ............... 8005141
Aug. 18, 1980 [GB] United Kingdom ............... 8026884

[51] Int. Cl.$^5$ ............... A01N 43/653; C07D 249/08
[52] U.S. Cl. ............................ 514/383; 548/267.8
[58] Field of Search ................ 548/262; 514/383, 184

[56] References Cited

U.S. PATENT DOCUMENTS

| | | | |
|---|---|---|---|
| 4,118,487 | 10/1978 | Regel, IV et al. ............... | 548/262 |
| 4,243,405 | 1/1981 | Balasubramanyan et al. ..... | 548/262 |
| 4,414,210 | 11/1983 | Miller et al. ............... | 548/262 |
| 4,620,011 | 10/1986 | Worthington et al. ........... | 548/262 |
| 4,654,332 | 3/1987 | Parry et al. ............... | 548/262 |

FOREIGN PATENT DOCUMENTS

| | | | |
|---|---|---|---|
| 0011768 | 6/1980 | European Pat. Off. ........... | 548/262 |
| 0011769 | 6/1980 | European Pat. Off. ........... | 548/262 |
| 0015756 | 9/1980 | European Pat. Off. ........... | 548/262 |
| 0019189 | 11/1980 | European Pat. Off. ........... | 548/262 |
| 2064520A | 6/1981 | United Kingdom ............... | 548/262 |

*Primary Examiner*—Richard L. Raymond
*Assistant Examiner*—Patricia L. Morris
*Attorney, Agent, or Firm*—Cushman, Darby & Cushman

[57] ABSTRACT

A compound of general formula (I):

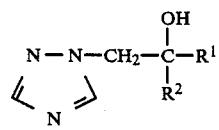

wherein $R^1$ is $C_{1-6}$ alkyl, cyclopropyl, cyclopentyl, cyclohexyl or phenyl, and $R^2$ is phenyl or benzyl; the phenyl or the phenyl moiety optionally substituted with halogen, $C_{1-5}$ alkyl, halo-$C_{1-4}$ alkyl, halo-$C_{1-4}$ alkoxy, nitro, phenyl, phenoxy, benzyl, optionally halo-substituted benzyloxy, alkylenedioxy; haloalkylenedioxy; amino, mono- or di-$C_{1-4}$ alkylamino, hydroxy, morpholino or carboxy or an alkyl ester thereof, and/or the alkyl moiety of the benzyl is optionally substituted with one $C_{1-4}$ alkyl; or an acid addition salt or metal complex thereof. The compounds are useful fungicides and plant growth regulating agents.

1 Claim, No Drawings

METHOD OF PREVENTING FUNGAL ATTACK ON WOOD, HIDES, LEATHER OR PAINT FILMS USING A TRIAZOLE

This is a continuation of application Ser. No. 579,012, filed Feb. 10, 1984, now U.S. Pat. No. 4,595,406 which is itself a division of Ser. No. 183,410, filed Sep. 3, 1980 and now U.S. Pat. No. 4,551,469 which is a continuation-in-part of Ser. No. 124,253, filed Feb. 25, 1980, now U.S. Pat. No. 4,654,332.

This invention relates to triazole compounds useful as fungicides and plant growth regulating agents, to a process for preparing them, to fungicidal and plant growth regulating compositions containing them, and to a method of combating fungal infections in, and regulating the growth of, plants using them.

The triazole compounds have the general formula (I):

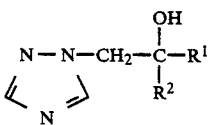

wherein $R^1$ is alkyl, cycloalkyl (e.g. cyclopropyl, cyclopentyl or cyclohexyl) or optionally substituted phenyl and $R^2$ is optionally substituted phenyl or optionally substituted benzyl; or an acid addition salt or metal complex thereof.

The compounds of the invention can contain chiral centres. Such compounds are generally obtained in the form of racemic mixtures. However, these and other mixtures can be separated into the individual isomers by methods known in the art.

The alkyl groups can be a straight or branched chain group having 1 to 6, e.g. 1 to 4, carbon atoms; examples are methyl, ethyl, propyl (n- or iso-propyl), butyl (n-, sec-, iso- or t-butyl), pentyl (e.g. n-pentyl) and hexyl (e.g. n-hexyl).

Examples of suitable substituents for the phenyl and for the phenyl moiety of the benzyl are halogen (e.g. fluorine, chlorine or bromine), $C_{1-5}$ alkyl /e.g. methyl, ethyl, propyl (n- or iso-propyl) and butyl (n-, sec-, iso- or t-butyl)/, $C_{1-4}$ alkoxy (e.g. methoxy and ethoxy), halo- $C_{1-4}$ alkyl (e.g. trifluoromethyl or 1,1,2,2-tetrafluoroethyl), halo- $C_{1-4}$ alkoxy (e.g. trifluoromethoxy or 1,1,2,2-tetrafluoroethoxy), nitro, phenyl, phenoxy, benzyl, benzyloxy (optionally ring substituted with halogen), alkylenedioxy, haloalkylenedioxy (e.g. difluoromethylenedioxy), amino, mono- or di- $C_{1-4}$ alkylamino (e.g. dimethylamino), hydroxy, morpholino and carboxy (and alkyl esters thereof). The alkyl moiety of the benzyl can be substituted with for example one alkyl (e.g. methyl or ethyl). Suitably the phenyl and benzyl are unsubstituted or substituted with 1, 2 or 3 ring substituents as defined above. Preferably the benzyl and phenyl have a single ring substituent in the o- or p-position. Examples of these groups are phenyl, benzyl, α-methylbenzyl, o-, m- or p-chlorophenyl, 2,4- or 2,6-dichlorophenyl, o-, m- or p-fluorophenyl, 2,4- or 2,6-difluorophenyl, o-, m- or p-bromophenyl, 2-chloro-4-fluorophenyl, 2-fluoro-4-chlorophenyl, 2-chloro-6-fluorophenyl, o-, m- or p-methoxyphenyl, 2,4-dimethoxyphenyl, o-, m- or p-ethoxyphenyl, o-, m- or p-nitrophenyl, 2-chloro-4-nitrophenyl, 2-chloro-5-nitrophenyl, o-, m-or p-methylphenyl, 2,4-dimethylphenyl, o-, m- or p-t-butylphenyl, o-, m- or p-trifluoromethylphenyl, o-, m-or p-trifluoromethoxyphenyl, o-, m- or p-(1,1,2,2-tetrafluoroethyl)phenyl, 2,3-(difluoromethylenedioxy)phenyl, 2-fluoro-4-methoxyphenyl, 2-methoxy-4-fluorophenyl, 2-methoxy-4-chlorophenyl, 2-methoxy-4-fluorophenyl, o-, m- or p-phenoxyphenyl, o-, m- or p-phenylphenyl (o-, m- or p-biphenylyl), o-, m-or p-benzylphenyl, o-, m- or p-benzyloxyphenyl, o-, m-or p-(p-chloro- or p-fluoro-benzyloxy)phenyl, o-, m-or p-aminophenyl, o-, m-or p-(N,N-dimethylamino)phenyl, o-, m- or p-hydroxyphenyl, o-, m- or p-carboxyphenyl, o-, m-or p-(methoxycarbonyl)phenyl, o-, m- or p-morpholinophenyl and the corresponding ring substituted benzyl and α-methylbenzyl groups.

The salts can be salts with inorganic or organic acids e.g. hydrochloric, nitric, sulphuric, acetic, p-toluenesulphonic or oxalic acid.

Suitably the metal complex is one including, as the metal, copper, zinc, manganese or iron. It preferably has the general formula:

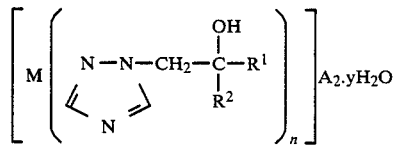

wherein Y, $R^1$ and $R^2$ are as defined above, M is a metal, A is an anion (e.g. a chloride, bromide, iodide, nitrate, sulphate or phosphate anion), n is 2 or 4 and y is 0 or an integer of 1 to 12.

Examples of the compounds of the invention are shown in Table I.

TABLE I

| COMPOUND NO | $R^1$ | $R^2$ | MELTING POINT (°C.) |
|---|---|---|---|
| 1 | $C_6H_5$— | $C_6H_5CH_2$— | 124–125° |
| 2 | $C_6H_5$— | p-Cl—$C_6H_4CH_2$— | 144–145° |
| 3 | $C_6H_5$— | p-F—$C_6H_4CH_2$— | 116–118° |
| 4 | p-Cl—$C_6H_4$— | p-Cl—$C_6H_4CH_2$— | 80–83° |
| 5 | p-Cl—$C_6H_4$— | $C_6H_5CH_2$— | 109–111° |
| 6 | p-F—$C_6H_4$— | $C_6H_5CH_2$— | 141–142° |
| 7* | $C_6H_5$— | 2,4-diCl—$C_6H_3CH_2$— | 104–106° |
| 8+ | p-F—$C_6H_4$— | p-F—$C_6H_4CH_2$— | 154–156° |
| 9 | p-F—$C_6H_4$— | p-Cl—$C_6H_4CH_2$— | 168–170° |
| 10 | t-Bu | $C_6H_5CH_2$— | 110–111° |
| 11 | t-Bu | p-Cl—$C_6H_4CH_2$ | 86–87° |
| 12 | t-Bu | p-F—$C_6H_4CH_2$— | 146–148° |
| 13 | $C_6H_5$— | o-F—$C_6H_4CH_2$— | 133–134° |
| 14 | p-Cl—$C_6H_4$— | o-F—$C_6H_4CH_2$— | 95–96° |
| 15 | $C_6H_5$— | o-Cl—$C_6H_4CH_2$ | 69–71° |
| 16 | p-MeO—$C_6H_4$— | $C_6H_5CH_2$ | 100–103° |
| 17 | $C_6H_5$— | $C_6H_5$— | 128–129° |

TABLE I-continued

| COMPOUND NO | R¹ | R² | MELTING POINT (°C.) |
|---|---|---|---|
| 18+ | p-F—$C_6H_4$— | p-F—$C_6H_4CH_2$— | 161–163° |
| 19 | $C_6H_5$— | 2,4-diCl—$C_6H_3CH_2$— | 104–106° |
| 20 | t-Bu | o-Cl—$C_6H_4CH_2$— | 74–75° |
| 21 | t-Bu | o-F—$C_6H_4CH_2$— | 96–98° |
| 22 | t-Bu | m-Cl—$C_6H_4CH_2$— | 88–89° |
| 23 | t-Bu | m-$CF_3$—$C_6H_4CH_2$— | 106–107° |
| 24 | $C_6H_5$— | p-t-Bu—$C_6H_4CH_2$— | 80–83° |
| 25 | p-Cl—$C_6H_4$— | $C_6H_5$— | 83–85° |
| 26 | p-Cl—$C_6H_4$— | p-Cl—$C_6H_4$— | 147–148° |
| 27 | p-Cl—$C_6H_4$— | p-F—$C_6H_4$— | 154–155° |
| 28 | 2,4-diCl—$C_6H_3$— | $C_6H_5$— | 191–194° |
| 29 | p-F—$C_6H_4$— | p-F—$C_6H_4$— | 170–171° |
| 30 | p-F—$C_6H_4$— | $C_6H_5$— | 139–140° |
| 31 | i-Bu | $C_6H_5$— | 94–95° |
| 32 | n-Bu | p-Cl—$C_6H_5$— | 95–97° |
| 33 | t-Bu | 2-Cl-6-F-$C_6H_3CH_2$— | |
| 34 | t-Bu | 2-Cl-4-F-$C_6H_3CH_2$— | 95° |
| 35 | t-Bu | 2-F-4-Cl-$C_6H_3CH_2$— | 104–106° |
| 36 | t-Bu | 2,4-diCl—$C_6H_3CH_2$— | |
| 37 | t-Bu | 2,6-diCl—$C_6H_3CH_2$— | |
| 38 | t-Bu | 2,6-diF—$C_6H_3CH_2$— | |
| 39 | t-Bu | m-$CF_3$—$C_6H_4CH_2$— | |
| 40 | $C_6H_5$— | p-t-Bu—$C_6H_4$ | 131–135° |
| 41 | $C_6H_5$— | o-Cl—$C_6H_4$— | |
| 42 | $C_6H_5$— | o-F—$C_6H_4$— | |
| 43 | p-Cl—$C_6H_4$— | o-Cl—$C_6H_4$— | 137–138° |
| 44 | p-Cl—$C_6H_4$— | o-F—$C_6H_4$— | 144–145° |
| 45 | p-F—$C_6H_4$— | o-Cl—$C_6H_4$— | 115–116° |
| 46 | p-F—$C_6H_4$— | o-F—$C_6H_4$— | 120–123° |
| 47 | $C_6H_5$— | o-$C_6H_5$O—$C_6H_4$— | |
| 48 | p-Cl—$C_6H_4$— | o-$C_6H_5$O—$C_6H_4$— | |
| 49 | $C_6H_5$— | o-Me—$C_6H_4$— | |
| 50 | p-Cl—$C_6H_4$— | o-Me—$C_6H_4$— | 157–158° |
| 51 | 2,4-diCl—$C_6H_3$— | p-F—$C_6H_4$— | 137–138° |
| 52 | o-Cl—$C_6H_4$— | p-MeO—$C_6H_4$— | 184–185° |
| 53 | 2,4-diCl—$C_6H_3$— | p-Cl—$C_6H_4$— | 174–175° |
| 54 | 2,4-diCl—$C_6H_3$— | o-Cl—$C_6H_4$— | 149–151° |
| 55 | 2,4-diCl—$C_6H_3$— | o-F—$C_6H_4$— | 146–147° |
| 56 | p-$C_6H_5CH_2$O—$C_6H_4$— | $C_6H_5$— | 134–136° |
| 57 | p-(p-Cl—$C_6H_4CH_2$O)—$C_6H_4$— | $C_6H_5$— | 98–100° |
| 58 | m-Cl—$C_6H_4$— | p-Cl—$C_6H_4$— | 139–142° |
| 59 | p-(p-F—$C_6H_4CH_2$O)—$C_6H_4$— | $C_6H_5$ | 105–107° |
| 60 | m-Cl—$C_6H_4$— | p-F—$C_6H_4$— | 190–193° |
| 61 | m-Cl—$C_6H_4$— | o-MeO—$C_6H_4$— | 58–60° |
| 62 | 2,4-diCl—$C_6H_3$— | m-Cl—$C_6H_4$— | 139–142° |
| 63 | o-Me—$C_6H_4$— | p-F—$C_6H_4$— | 200–201° |
| 64 | o-Me—$C_6H_4$— | p-Cl—$C_6H_4$— | 157–158° |
| 65 | o-Me—$C_6H_4$— | $C_6H_5$ | |
| 66 | o-Cl—$C_6H_4$— | $C_6H_5$ | |
| 67 | o-F—$C_6H_4$— | $C_6H_5$ | |
| 68 | o-Br—$C_6H_4$— | $C_6H_5$ | |
| 69 | o-Br—$C_6H_4$— | p-Cl—$C_6H_4$— | |
| 70 | o-Br—$C_6H_4$— | p-F—$C_6H_4$— | |
| 71 | p-$NO_2$—$C_6H_4$— | $C_6H_5$ | |
| 72 | 2-Cl-5-$NO_2$-$C_6H_3$— | $C_6H_5$ | |
| 73 | 2-Cl-4-$NO_2$-$C_6H_3$— | p-Cl—$C_6H_4$— | |
| 74 | o-$NH_2$—$C_6H_4$— | $C_6H_5$ | |
| 75 | p-Me—$C_6H_4$— | $C_6H_5$ | |
| 76 | o-$CO_2$H—$C_6H_4$— | p-F—$C_6H_4$— | |
| 77 | o-$CO_2$Me—$C_6H_4$— | p-F—$C_6H_4$— | |
| 78 | o-$CO_2$H—$C_6H_4$— | $C_6H_5$ | |
| 79 | o-$CO_2$Me—$C_6H_4$— | $C_6H_5$ | |
| 80 | o-OH—$C_6H_4$— | $C_6H_5$— | |
| 81 | o-MeO—$C_6H_4$— | $C_6H_5$ | |
| 82 | o-MeO—$C_6H_4$— | p-Cl—$C_6H_4$— | |
| 83 | o-MeO—$C_6H_4$— | p-F—$C_6H_4$— | |
| 84 | p-OH—$C_6H_4$— | $C_6H_5$— | |
| 85 | p-Br—$C_6H_4$— | $C_6H_5$— | |
| 86 | p-Br—$C_6H_4$— | p-Br—$C_6H_4$— | |
| 87 | p-Br—$C_6H_4$— | p-Cl—$C_6H_4$— | |
| 88 | p-$(CH_3)_2$N—$C_6H_4$— | $C_6H_5$— | |
| 89 | o-Me—$C_6H_4$— | p-Me—$C_6H_4$— | |
| 90 | o-Cl—$C_6H_4$— | p-Me—$C_6H_4$— | |
| 91 | o-F—$C_6H_4$— | p-Me—$C_6H_4$— | |
| 92 | o-Br—$C_6H_4$— | p-Me—$C_6H_4$— | |
| 93 | o-$NH_2$—$C_6H_4$— | p-Cl—$C_6H_4$— | |
| 94 | o-$CO_2$H—$C_6H_4$— | p-Me—$C_6H_4$— | |
| 95 | o-$CO_2$Me—$C_6H_4$— | p-Me—$C_6H_4$— | |
| 96 | p-MO—$C_6H_4$— | $C_6H_5$— | |

TABLE I-continued

| COMPOUND NO | $R^1$ | $R^2$ | MELTING POINT (°C.) |
|---|---|---|---|
| 97 | p-F—$C_6H_4$— | p-$NO_2$—$C_6H_4$— | |
| 98 | o-$CO_2H$—$C_6H_4$— | p-Br—$C_6H_4$— | |
| 99 | o-$CO_2Me$—$C_6H_4$— | p-Br—$C_6H_4$— | |
| 100 | o-$CO_2H$—$C_6H_4$— | p-Cl—$C_6H_4$— | |
| 101 | o-$CO_2Me$—$C_6H_4$— | p-Cl—$C_6H_4$— | |
| 102 | p-Me—$C_6H_4$— | p-Me—$C_6H_4$— | |
| 103 | 2,4-diMe—$C_6H_3$— | $C_6H_5$— | |
| 104 | m-$NO_2$—$C_6H_4$— | $C_6H_5$— | |
| 105 | o-Cl—$C_6H_4$— | o-Cl—$C_6H_4$— | |
| 106 | o-$CF_3$—$C_6H_4$— | $C_6H_5$— | |
| 107 | m-$CF_3$—$C_6H_4$— | $C_6H_5$— | |
| 108 | p-$CF_3$—$C_6H_4$— | $C_6H_5$— | |
| 109 | m-$CF_3$—$C_6H_4$— | p-Cl—$C_6H_4$— | |
| 110 | p-$OCF_3$—$C_6H_4$— | $C_6H_5$— | |
| 111 | p-$OCF_3$—$C_6H_4$— | p-Cl—$C_6H_4$— | |
| 112 | p-$OCF_3$—$C_6H_4$— | o-Cl—$C_6H_4$— | |
| 113 | p-$OCF_3$—$C_6H_4$— | p-$OCF_3$—$C_6H_4$— | |
| 114 | m-$OCF_3$—$C_6H_4$— | $C_6H_5$— | |
| 115 | m-$OCF_3$—$C_6H_4$— | p-Cl—$C_6H_4$— | |
| 116 | m-$OCF_3$—$C_6H_4$— | p-Br—$C_6H_4$— | |
| 117 | o-$OCF_2CHF_2$—$C_6H_4$— | $C_6H_5$— | |
| 118 | o-$OCF_2CHF_2$—$C_6H_4$— | p-Cl—$C_6H_4$— | |
| 119 | m-$OCF_2CHF_2$—$C_6H_4$— | $C_6H_5$— | |
| 120 | m-$OCF_2CHF_2$—$C_6H_4$— | p-Cl—$C_6H_4$— | |
| 121 | p-$OCF_2CHF_2$—$C_6H_4$— | $C_6H_5$— | |
| 122 | p-$OCF_2CHF_2$—$C_6H_4$— | p-Cl—$C_6H_4$— | |
| 123 | p-$OCF_2CHF_2$—$C_6H_4$— | p-$OCF_2CHF_2$—$C_6H_4$— | |
| 124 | 2,3-Z—$C_6H_4$— | $C_6H_5$— | |
| 125 | 2,3-Z—$C_6H_4$— | p-Cl—$C_6H_4$— | |
| 126 | 2,3-Z—$C_6H_4$— | o-Cl—$C_6H_4$— | |
| 127 | 2,3-Z—$C_6H_4$— | p-F—$C_6H_4$— | |
| 128 | t-Bu | o-Br—$C_6H_4CH_2$— | 111–115° |
| 129 | t-Bu | 2,4-diF—$C_6H_3CH_2$— | 140° |
| 130 | t-Bu | o-Meo—$C_6H_4CH_2$— | 113–116° |
| 131 | Me | $C_6H_5$— | |
| 132 | Me | p-Cl—$C_6H_4$— | |
| 133 | Me | 2,4-diCl—$C_6H_3$— | |
| 134 | Me | p-F—$C_6H_4$— | |
| 135 | Me | o-Cl—$C_6H_4$— | |
| 136 | Me | o-F—$C_6H_4$— | |
| 137 | Me | o-Me—$C_6H_4$— | |
| 138 | Me | 2,4-diMe—$C_6H_3$— | |
| 139 | Et | $C_6H_5$— | |
| 140 | Et | p-Cl—$C_6H_4$— | |
| 141 | Et | 2,4-diCl—$C_6H_3$— | |
| 142 | Et | p-F—$C_6H_4$— | |
| 143 | Et | o-Cl—$C_6H_4$— | |
| 144 | Et | o-F—$C_6H_4$— | |
| 145 | Me | o-Me—$C_6H_4$— | |
| 146 | Me | 2,4-diMe—$C_6H_3$— | |
| 147 | n-Pr | $C_6H_4$— | |
| 148 | n-Pr | p-Cl—$C_6H_4$— | |
| 149 | n-Pr | p-F—$C_6H_4$— | |
| 150 | n-Pr | 2,4-diCl—$C_6H_4$— | |
| 151 | n-Pr | o-Cl—$C_6H_4$— | |
| 152 | n-Pr | o-F—$C_6H_4$— | |
| 153 | n-Pr | o-Me—$C_6H_4$— | |
| 154 | n-Pr | 2,4-diMe—$C_6H_3$— | |
| 155 | n-Pr | p-MeO—$C_6H_4$— | |
| 156 | n-Pr | o-Meo—$C_6H_4$— | |
| 157 | i-Pr | $C_6H_5$— | |
| 158 | i-Pr | p-Cl—$C_6H_4$— | |
| 159 | i-Pr | p-F—$C_6H_4$— | |
| 160 | i-Pr | 2,4-diCl—$C_6H_3$— | |
| 161 | i-Pr | o-Cl—$C_6H_4$— | |
| 162 | i-Pr | o-F—$C_6H_4$— | |
| 163 | i-Pr | o-Me—$C_6H_4$— | |
| 164 | i-Pr | 2,4-diMe—$C_6H_3$— | |
| 165 | i-Pr | o-MeO—$C_6H_4$— | |
| 166 | i-Pr | p-MeO—$C_6H_4$— | |
| 167 | $C_3H_5$— | $C_6H_5$— | |
| 168 | $C_3H_5$— | p-Cl—$C_6H_4$— | |
| 169 | $C_3H_5$— | p-F—$C_6H_4$— | |
| 170 | $C_3H_5$— | 2,4-diCl—$C_6H_3$— | |
| 171 | $C_3H_5$— | o-Cl—$C_6H_4$— | |
| 172 | $C_3H_5$— | o-F—$C_6H_4$— | |
| 173 | $C_3H_5$— | o-Me—$C_6H_4$— | |
| 174 | $C_3H_5$— | 2,4-diMe—$C_6H_3$— | |
| 175 | $C_3H_5$— | o-MeO—$C_6H_4$— | |
| 176 | $C_3H_5$— | p-MeO—$C_6H_4$— | |
| 177 | n-Bu | $C_6H_5$— | |

TABLE I-continued

| COMPOUND NO | R¹ | R² | MELTING POINT (°C.) |
|---|---|---|---|
| 178 | n-Bu | p-F—$C_6H_4$— | |
| 179 | n-Bu | 2,4-diCl—$C_6H_3$— | |
| 180 | n-Bu | o-Cl—$C_6H_4$— | |
| 181 | n-Bu | o-F—$C_6H_4$— | |
| 182 | n-Bu | o-Me—$C_6H_4$— | |
| 183 | n-Bu | 2,4-diMe—$C_6H_3$— | |
| 184 | n-Bu | o-MeO—$C_6H_4$— | |
| 185 | n-Bu | p-MeO—$C_6H_4$— | |
| 186 | i-Bu | p-Cl—$C_6H_4$— | |
| 187 | i-Bu | p-F—$C_6H_4$— | |
| 188 | i-Bu | 2,4-diCl—$C_6H_3$— | |
| 189 | i-Bu | o-Cl—$C_6H_4$— | |
| 190 | i-Bu | o-F—$C_6H_4$— | |
| 191 | i-Bu | o-Me—$C_6H_4$— | |
| 192 | i-Bu | 2,4-diMe—$C_6H_4$— | |
| 193 | i-Bu | p-MeO—$C_6H_4$— | |
| 194 | i-Bu | o-Meo—$C_6H_4$— | |
| 195 | t-Bu | $C_6H_5$— | |
| 196 | t-Bu | p-Cl—$C_6H_4$— | |
| 197 | t-Bu | 2,4-diCl—$C_6H_4$— | |
| 198 | t-Bu | p-F—$C_6H_4$— | |
| 199 | t-Bu | o-Cl—$C_6H_4$— | |
| 200 | t-Bu | o-F—$C_6H_4$— | |
| 201 | t-Bu | o-Me—$C_6H_4$— | |
| 202 | t-Bu | 2,4-diMe—$C_6H_3$— | |
| 203 | t-Bu | o-MeO—$C_6H_4$— | |
| 204 | t-Bu | p-MeO—$C_6H_4$— | |
| 205 | n-Pe | $C_6H_5$— | |
| 206 | n-Pe | p-Cl—$C_6H_4$— | |
| 207 | n-Pe | 2,4-diCl—$C_6H_3$— | |
| 208 | n-Pe | p-F—$C_6H_4$— | |
| 209 | n-Pe | o-Cl—$C_6H_4$— | |
| 210 | n-Pe | o-F—$C_6H_4$— | |
| 211 | n-Pe | o-MeO—$C_6H_4$— | |
| 212 | n-Pe | 2,4-diMe—$C_6H_3$— | |
| 213 | n-Pe | o-MeO—$C_6H_4$— | |
| 214 | n-Pe | p-MeO—$C_6H_4$— | |
| 215 | $C_5H_9$ | $C_6H_5$ | |
| 216 | $C_5H_9$ | p-Cl—$C_6H_4$— | |
| 217 | $C_5H_9$ | 2,4-diCl—$C_6H_3$— | |
| 218 | $C_5H_9$ | p-F—$C_6H_4$— | |
| 219 | $C_5H_9$ | o-Cl—$C_6H_4$— | |
| 220 | $C_5H_9$ | o-F—$C_6H_4$— | |
| 221 | $C_5H_9$ | o-Me—$C_6H_4$— | |
| 222 | $C_5H_9$ | p-Me—$C_6H_4$— | |
| 223 | $C_5H_9$ | o-MeO—$C_6H_4$— | |
| 224 | $C_5H_9$ | p-MeO—$C_6H_4$— | |
| 225 | n-He | $C_6H_5$— | |
| 226 | n-He | p-Cl—$C_6H_4$— | |
| 227 | n-He | 2,4-diCl—$C_6H_3$— | |
| 228 | n-He | p-F—$C_6H_4$— | |
| 229 | n-He | o-Cl—$C_6H_4$— | |
| 230 | n-He | o-F—$C_6H_4$— | |
| 231 | n-He | o-Me—$C_6H_4$— | |
| 232 | n-He | 2,4-diMe—$C_6H_3$— | |
| 233 | n-He | o-MeO—$C_6H_4$— | |
| 234 | n-He | p-MeO—$C_6H_4$— | |
| 235 | $C_6H_{11}$ | $C_6H_5$— | |
| 236 | $C_6H_{11}$ | p-Cl—$C_6H_4$— | |
| 237 | $C_6H_{11}$ | 2,4-diCl—$C_6H_4$— | |
| 238 | $C_6H_{11}$ | p-F—$C_6H_4$— | |
| 239 | $C_6H_{11}$ | o-Cl—$C_6H_4$— | |
| 240 | $C_6H_{11}$ | o-F—$C_6H_4$— | |
| 241 | $C_6H_{11}$ | o-Me—$C_6H_4$— | |
| 242 | $C_6H_{11}$ | 2,4-diMe—$C_6H_3$— | |
| 243 | $C_6H_{11}$ | o-MeO—$C_6H_4$— | |
| 244 | $C_6H_{11}$ | p-MeO—$C_6H_4$— | |
| 245 | t-Bu | 2-F-4-MeO—$C_6H_3CH_2$— | |
| 246 | t-Bu | 2-MeO-4-F—$C_6H_3CH_2$— | |
| 247 | t-Bu | 2-MeO-4-Cl—$C_6H_3CH_2$— | |
| 248 | t-Bu | 2-MeO-4-F—$C_6H_3CH_2$— | |
| 249 | t-Bu | p-$CF_3$—$C_6H_4CH_2$— | |
| 250 | $C_6H_5$— | o-$C_6H_5$—$C_6H_4$— | |

TABLE I-continued

| COMPOUND NO | R$^1$ | R$^2$ | MELTING POINT (°C.) |
|---|---|---|---|
| 251 | p-ClC$_6$H$_4$— | o-C$_6$H$_5$—C$_6$H$_4$— | |

*Includes 1 mole of ethanol occluded in the crystal lattice.
+Compounds 8 and 18 were obtained as polymorphs and this explains their different melting points.
n-Pe = n-Pentyl
n-He = n-hexyl
C$_3$H$_5$ = cyclopropyl
C$_5$H$_9$ = cyclopentyl
C$_6$H$_{11}$ = cyclohexyl
MO = morpholino
Z = difluoromethylenedioxy.

$$Y-Mg-R^1 \qquad Y-Mg-R^2$$
$$(Va) \qquad\qquad (Vb)$$

wherein R$^1$ and R$^2$ are as defined above and Y is a halogen (preferably chlorine, bromine or iodine) in a convenient solvent such as diethyl ether or tetrahydrofuran. Generally a mixture of the compounds of general formula (II) and (III) are obtained. For example, when a compound of general formula (IVa) wherein R$^1$ is alkyl or cycloalkyl is reacted, the compound of formula (II) generally predominates in the mixture; on the other hand, when R$^1$ is optionally substituted phenyl, the compound of general formula (III) generally predominates in the mixture.

The compounds of general formula (IV) and (V) may be made by methods set out in the literature.

The compounds of general formula (II) wherein each of R$^1$ and R$^2$, which may be the same or different, is substituted phenyl may also be prepared by reacting the appropriate benzophenone compound of general formula (VI)

$$R^1-CO-R^2$$

wherein R$^1$ and R$^2$ are as defined above, with dimethyl oxosulphonium methylide (Corey and Chaykovsky JACS, 1965, 87, 1353-1364) or dimethyl sulphonium methylide (Corey and Chaykovsky, JACS, 1962, 84, 3782) using methods set out in the literature.

The benzophenone compounds of general formula (VI) can be prepared, using the Friedel-Crafts reaction, by reacting a substituted benzoyl chloride with the appropriately substituted benzene in the presence of a Lewis acid e.g. aluminium chloride.

The compounds of general formula (II) wherein each of R$^1$ is alkyl, cycloalkyl or optionally substituted phenyl and R$^2$ is optionally substituted phenyl or optionally substituted benzyl can also be produced by reacting a β-hydroxy selenide compound of general The compounds of general formula (I) may be produced by reacting a compound of general formula (II) or (III):

<p align="center">(II) structure: epoxide CH$_2$—C(R$^1$)(R$^2$)—O ; (III) structure: X—CH$_2$—C(OH)(R$^1$)(R$^2$)</p> in which R$^1$ and R$^2$ are as defined above and X is a halogen atom (preferably a chlorine or bromine atom), with 1,2,4-triazole either in the presence of an acidbinding agent or in the form of one of its alkali metal salts in a convenient solvent. Suitably the compound of general formula (II) or (III) is reacted at 20°-100° C. with the sodium salt of 1,2,4-triazole (the salt can be prepared by adding either sodium hydride or sodium methoxide to 1,2,4-triazole) in a convenient solvent such as acetonitrile, methanol, ethanol or dimethylformamide. The product can be isolated by pouring the reaction mixture into water and recrystallising the solid formed from a convenient solvent.

The compounds of general formula (II) and (III) can be prepared by reacting a compound of general formula (IVa) or (IVb):

$$X-CH_2-\overset{O}{\overset{\|}{C}}-R^1 \qquad X-CH_2-\overset{O}{\overset{\|}{C}}-R^2$$
$$(IVa) \qquad\qquad (IVb)$$

wherein R$^1$, R$^2$ and X are as defined above with, respectively, a Grignard compound of general formula (Va) or (Vb):

$$CH_3-Se-CH_2-\underset{R^2}{\overset{R^1}{\underset{|}{\overset{|}{C}}}}-OH \qquad (VII)$$

wherein R$^1$ and R$^2$ are as defined above, with methyl iodide in potassium t-butoxide according to the method of Van Ende, Dumont and Krief, Angew. Chem. Int. Ed., 1975, 14, 700.

The β-hydroxy selenide compound can be prepared by treating the diselenide with the appropriate ketone in the presence of butyl lithium.

The compounds of general formula (III) wherein R$^1$ is alkyl or cycloalkyl and R$^2$ is optionally substituted benzyl (particularly benzyl ring substituted with alkoxy) can also be prepared by reacting a compound of general formula (VIII)

$$ArSCH_2-\underset{R^2}{\overset{OH}{\underset{|}{\overset{|}{C}}}}-R^1 \qquad (VIII)$$

wherein R$^1$ and R$^2$ are as defined above and Ar is aryl (e.g. phenyl) with an alkylating agent to give the corresponding sulphonium salt which is then reacted with 1,2,4-triazole in the form of an alkali metal (e.g. sodium or potassium) salt. The compound of general formula (VIII) can be prepared by methods known in the art.

The salts and metal complexes of the compounds of general formula (I) can be prepared from the latter in known manner. For example, the complexes can be made by reacting the uncomplexed compound with a metal salt in a suitable solvent.

The compounds of general formula (I) are generally prepared by the above reactions in the form of racemic mixtures. The resolution of these mixtures into the constituent enantiomers can be performed by known methods. Examples of these methods are (1) forming the diastereoisomeric salts or esters of the compound of general formula (I) with an optically active acid (e.g. camphor sulphonic acid), separating the isomeric salts or esters and converting the separated isomeric salts or esters into the enantiomers of the compound of general formula (I); (2) forming the diastereoisomeric carbamates of the compound of general formula (I) by reacting a halo-formate (e.g. chloroformate) of the latter with an optically active amine (e.g. α-methylbenzylamine), separating the isomeric carbamates, and converting the separated isomeric carbamates into the enantiomers of the compound of general formula (I); (3) forming the hemiphthate of the compound of general formula (I), reacting the hemiphthate with an optically active amine (e.g. α-methylbenzylamine) to give a salt of the hemiphthate, separating the isomeric salts and converting the separated salts into the enantiomers of the compound of general formula (I); or (4) resolving the mixtures using enantioselective crystallisation techniques (Leigh, Chemistry and Industry, 1970, pages 1016–1017, and ibid, 1977, page 36). The separation of the diastereoisomeric salts, esters and carbamates can be achieved by for example crystallisation techniques or by high pressure liquid chromatography (HPLC). Alternatively, the enantiomers can be prepared directly from the compound of general formula (II) by stereospecific reduction, for example by biochemical reduction (using for example yeast or *Aspergillus niger*) or by hydrogenation using chiral catalysts (e.g. a Wilkinson's catalyst) or by reduction with borohydride/amino acid complexes.

The compounds, salts and metal complexes are active fungicides, particularly against the diseases:

*Piricularia oryzae* on rice

*Puccinia recondita, Puccinia striiformis* and other rusts on wheat, *Puccinia hordei, Puccinia striiformis* and other rusts on barley, and rusts on other hosts e.g. coffee, apples, vegetables and ornamental plants

*Plasmopara viticola* on vines

*Erysiphe graminis* (powdery mildew) on barley and wheat and other powdery mildews on various hosts such as *Sphaerotheca fuliginea* on cucurbits (e.g. cucumber), *Podosphaera leucotricha* on apples and *Uncinula necator* on vines

*Helminthosporium* spp. and *Rhynchosporium* spp. on cereals

*Cercospora arachidicola* on peanuts and other *Cercospora* species on for example sugar beet, bananas and soya beans

*Botrytis cinerea* (grey mould) on tomatoes, strawberries, vines and other hosts

*Phytophthora infestans* (late blight) on tomatoes

*Venturia inaequalis* (scab) on apples

Some of the compounds have also shown a broad range of activities against fungi in vitro. They have activity against various post-harvest diseases on fruit (e.g. *Penicillium digatatum* and *italicum* on oranges and *Gloeosporium musarum* on bananas). Further some of the compounds are active as seed dressings against: Fusarium spp., Septoria spp., Tilletia spp. (i.e. bunt, a seed borne disease of wheat), Ustilago spp., Helminthosporium spp. on cereals, *Rhizoctonia solani* on cotton and *Corticium sasakii* on rice.

The compounds can move acropetally in the plant tissue. Moreover, the compounds can be volatile enough to be active in the vapour phase against fungi on the plant.

They may also be useful as industrial (as opposed to agricultural) fungicides, e.g. in the prevention of fungal attack on wood, hides, leather and especially paint films.

The compounds can also have plant growth regulating activities.

The plant growth regulating effects of the compounds are manifested as for example a stunting or dwarfing effect on the vegetative growth of woody and herbaceous mono- and di-cotyledonous plants. Such stunting or dwarfing may be useful, for example, in peanuts, cereals and soya bean where reduction in stem growth may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata*, *Festuca* spp. (e.g. *Festuca rubra*) and *Poa* spp. (e.g. *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in for example grasses. The compounds can also stunt weed species present in the grasses; examples of such weed species are sedges (e.g. *Cyperus* spp.) and dicotyledonous weeds (e.g. daisy, plantain, knotweed, speedwell, thistle, docks and ragwort). The growth of non-crop vegetation (e.g. weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful for example for improving the quality of a sward by preferential suppression of the growth of undesirable species.

The dwarfing may also be useful in miniaturising ornamental, household, garden and nursery plants (e.g. poinsettias, chrysanthemums, carnations, tulips and daffodils).

As indicated above, the compounds can also be used to stunt woody species. This property can be used to control hedgerows or to shape fruit trees (e.g. apples). Some coniferous trees are not significantly stunted by the compounds so the compounds could be useful in controlling undesirable vegetation in conifer nurseries.

The plant growth regulating effect may (as implied above) manifest itself in an increase in crop yield.

In the potato, vine control in the field and inhibition of sprouting in the store may be possible.

Other plant growth regulating effects caused by the compounds include alteration of leaf angle and promotion of tillering in monocotyledonous plants. The former effect may be useful for example in altering the leaf orientation of, for example, potato crops thereby letting more light into the crops and inducing an increase in phytosynthesis and tuber weight. By increasing tillering in monocotyledonous crops (e.g. rice), the number of flowering shoots per unit area may be increased thereby increasing the overall grain yield of such crops. In grass swards an increase in tillering could lead to a denser sward which may result in increased resilience in wear.

The treatment of plants with the compounds can lead to the leaves developing a darker green colour.

The compounds may inhibit, or at least delay, the flowering of sugar beet and thereby may increase sugar yield. They may also reduce the size of sugar beet without reducing significantly the sugar yield thereby enabling an increase in planting density to be made. Similarly in other root crops (e.g. turnip, swede, mangold, parsnip, beetroot, yam and cassava) it may be possible to increase the planting density.

The compounds could be useful in restricting the vegetative growth of cotton thereby leading to an increase in cotton yield.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below the snow cover during the cold weather. Further the compounds may cause drought or cold resistance in certain plants.

When applied as seed treatments at low rates the compounds can have a growth stimulating effect on plants.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. However, on certain plants even application rates within these ranges may give undesired phytotoxic effects. Routine tests may be necessary to determine the best rate of application of a specific compound for any specific purpose for which it is suitable.

The compounds may be used as such for fungicidal or plant growth regulating purposes but are more conveniently formulated into compositions for such usage. The invention thus provides also a fungicidal or plant growth regulating composition comprising a compound which is an enantiomer of the invention or an ester, salt or complex thereof, and a carrier or diluent.

The invention also provides a method of combating fungal diseases in a plant, which method comprises applying to the plant, to seed of the plant or to the locus of the plant or seed a compound which is an enantiomer of the invention or an ester, salt or complex thereof.

It also provides a method of regulating the growth of a plant, which method comprises applying to the plant, to seed of the plant or to the locus of the plant or seed a compound which is an enantiomer of the invention or an ester, salt or complex thereof as hereinbefore defined.

The compounds can be applied in a number of ways, for example they can be formulated or unformulated, directly to the foliage of a plant, to seeds or to other medium in which plants are growing or are to be planted, or they can be sprayed on, dusted on or applied as a cream or paste formulation, or they can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form.

By including suitable additives, for example additives for improving the distribution, adhesive power and resistance to rain on treated surfaces, the different compositions can be better adapted for various utilities.

The compounds can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound. The invention therefore also provides a fertiliser composition comprising a compound as hereinbefore defined.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butyl-naphthalene sulphonate, and a mixture of sodium diisopropyl and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient(s). These concentrates suitably contain organic acids (e.g. alkaryl or aryl sulphonic acids such as xylenesulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, e.g. compounds having similar or complementary fungicidal or plant growth regulating activity or compounds having herbicidal or insecticidal activity.

The other fungicidal compound can be for example one which is capable of combating ear diseases of cereals (e.g. wheat) such as Septoria, Gibberella and Helminthosporium spp., seed and soil borne diseases and downy and powdery mildews on grapes and powdery mildew and scab on apple etc. These mixtures of fungicides can have a broader spectrum of activity than the compound of general formula (I) alone; further the other fungicide can have a synergistic effect on the fungicidal activity of the compound of general formula (I). Examples of the other fungicidal compound are imazalil, benomyl, carbendazim, thiophanate-methyl, captafol, captan, sulphur, triforine, dodemorph, tridemorph, pyrazophos, furalaxyl, ethirimol, dimethirimol, bupirimate, chlorothalonil, vinclozolin, procymidone, iprodione, metalaxyl, forsetyl-aluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazitine, dodine, fentin acetate, fentin hydroxide, dinocap, folpet, dichlofluanid, ditalimphos, kitazin, cycloheximide, dichlobutrazol, a dithiocarbamate, a copper compound, a mercury compound, DPX 3217, RH 2161, Chevron RE 20615, CGA 64250, CGA 64251 and RO 14-3169.

The compounds of general formula (I) can be mixed with soil, peat or other rooting media for the protection of plants against seed-borne, soil-borne or foliar fungal diseases.

Suitable insecticides are pirimor, croneton, dimethoate, metasystox and formothion.

The other plant growth regulating compound can be one which controls weeds or seedhead formation, improves the level or longevity of the plant growth regulating activity of the compounds of general formula (I), selectively controls the growth of the less desirable plants (e.g. grasses) or causes the compound of general formula (I) to act faster or slower as a plant growth regulating agent. Some of these other agents will be herbicides. Examples of suitable agents are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or BAP), phenoxyacetic acids, (e.g. 2,4-D or MCPA), pyridyloxyphenoxypropionic acids substituted benzoic acids (e.g. TIBA), morphactins (e.g. chlorfluorecol), maleic hydrazide, glyphosate, glyphosine, long chain fatty alcohols and acids (e.g. Off Shoot O or Off Shoot T), dikegulac, Sustar, Embark, substituted quaternary ammonium and phosphonium compounds (e.g. CCC, mepiquat chloride or Phosfon-D), Ethrel, carbetamide, Racuza, Alar, asulam, abscissic acid, ancymidol (and its analogues e.g. isopyrimol), RH531, hydroxybenzonitriles (e.g. bromoxynil), Avenge, Suffix, Lontrel or thiocarbamates (e.g. Eptam).

, The following Examples illustrate the invention; the temperatures are given in degrees Centigrade (°).

EXAMPLE 1

1-(1,2,4-Triazol-1-yl)-2,3-diphenyl-propan-2-ol

Benzyl chloride (0.2 mol) was dissolved in dry diethyl ether (200 ml) and added dropwise to magnesium turnings (0.22 g atoms). After all the magnesium had reacted, the solution was refluxed for 1 hour and cooled to room temperature. Phenacyl chloride (0.1 mol) in dry diethyl ether (100 ml) was added dropwise over 1 hour at such a rate as to maintain gentle reflux. The solution was then refluxed for 2 hours, and cooled to room temperature; the mixture was poured into ice and the complex decomposed with ammonium chloride solution. The ethereal solution was washed several times with water (2×200 ml), dried ($Na_2SO_4$), and the solvent removed in vacuo to give, as a colourless oil, the crude chlorohydrin which was dissolved in dimethyl formamide (80 ml) and a solution of sodium triazole [prepared from sodium (0.1 g atoms) in methanol (40 ml) and 1,2,4-triazole (0.1 mol)] added dropwise at room temperature. After stirring at room temperature for 2 hours, the solution was warmed at 50° for 3 hours. The solvent was removed in vacuo and the residue poured into water to give a crystalline solid which was recrystallised from ethanol/petroleum ether to give the title compound, m.p. 124.5°.

EXAMPLE 2

1-(1,2,4-Triazol-1-yl)-2-phenyl-3-p-fluorophenyl-propan-2-ol p-Fluorobenzyl chloride (0.1 mol) in dry diethyl ether (100 ml) was added dropwise to magnesium turnings (0.11 g atoms) and the solution stirred vigorously until refluxing occurred. When all the magnesium had reacted, the solution was refluxed for a further 1 hour and then cooled to room temperature. Phenacyl chloride (0.05 mol) in dry diethyl ether (50 ml) was added dropwise to the solution over 1 hour at such a rate as to maintain gentle reflux. The mixture was refluxed for 2 hours, cooled to room temperature and the mixture poured into ice/ammonium chloride solution to decompose the complex. The ethereal solution was washed several times with water (2×200 ml), dried ($Na_2SO_4$), and the solvent removed in vacuo to give, as a colourless oil, the crude chlorohydrin. The latter was dissolved in dimethylformamide (40 ml) and a solution of sodium triazole [prepared from sodium (0.05 g atoms) in methanol (20 ml) and 1,2,4-triazole (0.05 mol)] added dropwise at room temperature. After stirring at room temperature for 2 hours, the solution was warmed at 50° for 3 hours. The solvent was removed in vacuo and the mixture poured into water to give a crystalline solid which was recrystallised from petroleum ether/chloroform to give the title compound, m.p. 116°–8°.

EXAMPLE 3

1,1-Diphenyl-2-(1,2,4-triazol-1-yl)-ethan-1-ol (Compound 17)

Stage 1. Bromobenzene (0.2 mol, 31.4 g) in sodium dry diethyl ether (200 ml) was added dropwise to magnesium (0.22 gram atoms, 5.3 g). After all the magnesium had reacted, phenacyl chloride (0.1 mol, 15.5 g) in diethyl ether (100 ml) was added dropwise and the solution stirred at room temperature for 1 hour. The reaction mixture was poured into saturated ammonium chloride solution, washed with water (3×150 ml), and dried ($Na_2SO_4$). Removal of the ether gave a pale yellow oil which solidified on standing. Recrystallisation from petroleum ether (60°–80°) gave 1,1-diphenyl-2-chloroethan-1-ol (60%) as a white crystalline solid, m.p. 56°–57°.

Stage 2. 1,2,4-Triazole (0.03 mol, 2.07 g) was added portionwise to a suspension of sodium hydride (0.03 mol, 0.72 g) in DMF (30 ml) and the solution stirred until effervescence ceased. 1,1-Diphenyl-2-chloroethan-1-ol (0.015 mol, 2.94 g) in dimethylformamide (DMF; 10 ml) was added dropwise and the solution warmed at 100° for six hours. The reaction mixture was poured into water and a white solid crystallised out. This was filtered off, washed with water, dried, and recrystallised from ethanol to give the title compound as a white crystalline solid, m.p. 128°–129°.

EXAMPLE 4

2-Methyl-4-phenyl-5-(1,2,4-triazol-1-yl)-pentan-4-ol (Compound 31)

Stage 1. The Grignard reagent generated from isobutyl bromide (0.1 mol, 13.7 g) in sodium dry diethyl ether (50 ml) and magnesium turnings (0.11 g atoms; 2.6 g) was added dropwise to a solution of phenacyl chloride (0.05 mol, 7.7 g) in sodium dry diethyl ether (100 ml) so that gentle reflux was maintained. The solution was then stirred at room temperature for 1 hour and the magnesium complex destroyed by pouring into a saturated ammonium chloride solution (200 ml). The ethereal extract was washed with water (3×150 ml) and dried ($Na_2SO_4$). Removal of the solvent gave a colourless liquid which distilled at reduced pressure to give 2-methyl-4-phenyl-5-chloro-pentan-4-ol (70%), b.p. 86°–88°/0.01 mm Hg.

Stage 2. 1,2,4-Triazole (0.03 mol, 2.07 g) was added portionwise to 100% sodium hydride (0.03 mol, 0.72 g) in dry DMF (30 ml) and stirred at room temperature until the effervescence ceased. 2-Methyl-4-phenyl-5-chloropentan-4-ol (0.01 mol, 2.1 g) in dry DMF (10 ml) was added dropwise at room temperature and then the solution was stirred at 100° for 6 hours. On cooling to room temperature the solution was poured into water to precipitate out a solid which was recrystallised from petroleum (60°–80°)/chloroform giving the title compound (60%) as a white crystalline solid, m.p. 94°–95°.

EXAMPLE 5

1-(1,2,4-Triazol-1-yl)-2-o-chlorophenyl-2-p-fluorophenyl-ethan-2-ol (Compound 45)

A solution of dimethyl oxosulphonium methylide was prepared under nitrogen from sodium hydride (0.03 mol) and powdered trimethyl oxosulphonium iodide (0.03 mol) in dry dimethylsulphoxide (DMSO; 30 ml). A solution of o-chlorophenyl p-fluorophenyl ketone (0.025 mol) in DMSO (10 ml) was added dropwise at room temperature. The solution was then heated at 50° for 1½ hours, cooled to room temperature and poured into water. The solution was extracted with diethyl ether (100 ml), washed with water (3×100 ml), and dried over anhydrous sodium sulphate. Removal of the solvent gave 1-o-chlorophenyl-1-p-fluorophenyl ethylene oxide (90%) as a colourless liquid.

1,2,4-Triazole (0.04 mol) was added portionwise to sodium hydride (0.04 mol) in DMF (40 ml) and the solution stirred at room temperature until effervescence ceased. 1-o-Chlorophenyl-1-p-fluorophenyl ethylene oxide (0.02 mol) in DMF (10 ml) was added dropwise and the solution stirred at 80° for 4 hours. The solution was poured into water and triturated with petroleum ether to give a white crystalline solid which was filtered off and dried. Recrystallisation from petroleum ether (60°–80°)/methylene chloride gave the title compound (70%) as a white crystalline solid, m.p. 115°–116°.

EXAMPLE 6

2,2-Dimethyl-3-(o-methoxybenzyl)-3-(1,2,4-triazol-1-yl)-butan-3-ol (Compound 130)

Stage 1

Potassium t-butoxide (19 g) was dissolved in dimethylsulphoxide (200 ml; dried by distilling from calcium hydride and sodamide) and pinacolone (15 g; freshly distilled from calcium hydride) was added under argon to give a yellow solution. o-Methoxyphenyl iodide (10 g) was then added and a brown colour rapidly developed. The solution was stirred for 1½ hours before pouring into water (1 liter), acidifying the mixture with 2M hydrochloric acid and extracting it with diethyl ether. Evaporation of the dried (MgSO$_4$) ethereal solution gave a yellow liquid (11.8 g) b.p. 88°–93° C./0.9 mm. The distillate solidified to give 2,2-dimethyl-4-(o-methoxyphenyl)butan-3-one (6 g).

Stage 2

Thioanisole (3.3 g) was added to diazobicyclooctane (3.5 g) in dry tetrahydrofuran (THF) under argon and the colourless solution was cooled in an ice/salt bath. 1.6M-butyl lithium solution (20 ml) in hexane was then added over 10 minutes at 0° to 2° C. After stirring the yellow solution for 15 minutes, a solid was precipitated. The mixture was stirred for a further 45 minutes in the ice bath and then it was allowed to warm up to room temperature. The mixture was then cooled in the ice bath and a solution of the product (5 g) of stage 1 in dry THF (25 ml) was added at 0° to 5° C. When the addition was complete, the resultant yellow solution was allowed to stand overnight, poured into water, acidified with 2M-hydrochloric acid and extracted with diethyl ether. The ethereal solution was washed well with water, dried (MgSO$_4$) and evaporated to give a yellow liquid (8.8 g) which solidified on standing. Recrystallisation from petroleum ether (60°–80°) gave 2,2-dimethyl-3-hydroxy-3-(o-methoxybenzyl)-4-thiophenylbutane (3.1 g), m.p. 74°–75° C.

Stage 3

The product (2.5 g) of Stage 2 was added to a stirred suspension of trimethyl oxonium tetrafluoroborate (1.3 g) in methylene chloride (25 ml). After about 1 hour a clear solution was obtained. The solvent was then removed on the rotavaporator to give a pale orange gum, which was dissolved in dry DMF (10 ml) and the solution added to a solution of 1,2,4-triazole sodium salt (1.2 g) in DMF (15 ml). [The solution was prepared by washing sodium hydride with dry diethyl ether, suspending it in dry DMF and adding the triazole]. The reaction mixture was then stirred at 120° C. for 2½ hours. The reaction mixture was then quenched by pouring into water (100 ml) and the emulsion was extracted with diethyl ether (3×50 ml). The ethereal solution was washed well with water, dried (MgSO$_4$) and evaporated to give a pale yellow liquid. The mixture was subjected to dry column chromatography on silica eluting with diethyl ether to give a colourless liquid which solidified on trituration with diethyl ether. Recrystallation from petroleum ether (60°–80°) gave the title compound (0.5 g; 23%), m.p. 113°–116°.

EXAMPLE 7

The compounds were tested against a variety of foliar fungal diseases of plants. The technique employed was as follows.

The plants were grown in John Innes Potting Compost (No. 1 or 2) in 4 cm diameter minipots. A layer of fine sand was placed at the bottom of the pots containing the dicotyledonous plants to facilitate uptake of test compound by the roots. The test compounds were formulated either by bead milling with aqueous Dispersol T or as a solution in acetone or acetone/ethanol which was diluted to the required concentration immediately before use. For the foliage diseases, suspensions (100 ppm active ingredient) were sprayed on to the soil. Exceptions to this were the tests on *Botrytis cinerea*, *Plasmopara viticola* and *Venturia inaequalis*. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the diseases. An exception was the test on *Erysiphe graminis* in which the plants were inoculated 24 hours before treatment. After inoculation, the plants were put into an appropriate environment to allow infection to take place and then incubated until the disease was ready for assessment. The period between inoculation and assessment varied from four to fourteen days according to the disease and environment.

The disease control was recorded by the following grading:

4=no disease
3=trace - 5% of disease on untreated plants
2=6–25% of disease on untreated plants
1=26–59% of disease on untreated plants
0=60–100% of disease on untreated plants The results are shown in Table II.

TABLE II

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INEQUALIS (APPLE) |
|---|---|---|---|---|---|---|---|---|
| 1 | 4 | 4 | 1 | 0 | 0 | 3 | 4 | 3 |
| 2 | 4 | 4 | 0 | 0 | 0 | 3 | 3 | |
| 3 | 4 | 4 | 1 | 0 | 0 | 3 | 4 | 3 |
| 4 | 3 | 4 | 0 | 4 | 0 | 3 | 4 | 3 |
| 5 | 4 | 4 | 1 | 4 | 0 | 3 | 3 | 4 |
| 6 | 4 | 4 | 3 | 2 | 0 | 3 | 4 | |
| 8 | 4 | | 3 | 4 | 3 | 3 | 4 | 3 |
| 9 | 3 | 4 | 2 | 0 | 0 | 2 | 3 | 3 |
| 10 | 4 | 4 | 3 | 0 | | 3 | 4 | 4 |
| 11 | 4 | 4 | 3 | 0 | 1 | 4 | 4 | 4 |
| 12 | 4 | 4 | | 0 | 0 | 4 | 4 | 4 |
| 13 | 4 | 4 | 3 | 3 | 0 | 3 | 4 | 3 |

TABLE II-continued

| COMPOUND NUMBER | PUCCINIA RECONDITA (WHEAT) | ERYSIPHE GRAMINIS (BARLEY) | PIRICULARIA ORYZAE (RICE) | PLASMOPARA VITICOLA (VINE) | PHYTOPHTHORA INFESTANS (TOMATO) | BOTRYTIS CINEREA (TOMATO) | CERCOSPORA ARACHIDICOLA (PEANUT) | VENTURIA INEQUALIS (APPLE) |
|---|---|---|---|---|---|---|---|---|
| 14 | 4 | 4 | 1 | 0 | 1 | 4 | 4 | 3 |
| 15 | 4 | 4 | 1 | 0 | 2 | 3 | 4 | 3 |
| 16 | 4 | 4 | 4 | 0 | 0 | 3 | 4 | 0 |
| 17 |   | 4 |   | 0 | 0 | 1 | 4 | 4 |
| 18 | 4 |   | 3 | 0 | 0 | 3 | 4 | 3 |
| 19 | 4 | 4 | 3 | 3 | 0 |   | 4 | 4 |
| 20 | 4 | 4 | 4 | 0 | 0 | 3 | 4 | 3 |
| 21 | 4 | 4 | 3 | 1 | 0 | 4 | 4 | 4 |
| 22 | 4 | 4 | 4 | 0 | 2 | 3 | 4 | 4 |
| 23 | 4 | 4 | 3 | 0 | 0 | 3 | 4 | 4 |
| 24 |   | 4 | 3 | 2 | 0 | 0 | 0 | 2 |
| 25 | 4 | 4 | 2 | 0 | 0 | 3 | 4 | 4 |
| 26 | 3 | 4 | 2 | 4 | 0 | 3 | 4 | 4 |
| 27 | 4 | 4 | 3 | 1 | 0 | 4 | 4 | 4 |
| 28 | 4 | 4 | 2 | 0 | 0 | 4 |   |   |
| 29 |   | 4 | 3 | 0 | 0 | 3 | 4 | 4 |
| 30 |   | 4 | 3 | 0 | 0 | 3 | 4 | 4 |
| 31 | 4 | 4 | 2 | 0 | 0 | 0 | 3 | 4 |
| 32 | 3 | 4 | 0 |   | 0 | 2 | 4 | 4 |
| 34 | 4 | 3 | 4 | 2 | 0 |   | 4 | 4 |
| 35 | 4 | 4 |   | 0 | 0 | 3 | 4 | 4 |
| 40 | 3 | 4 | 2 | 0 | 1 | 0 | 4 | 4 |
| 43 | 4 | 4 |   | 0 | 0 | 2 | 4 | 4 |
| 44 | 4 | 3 | 4 | 1 | 0 |   | 4 | 4 |
| 45 | 4 | 4 |   | 0 | 0 | 2 | 4 | 4 |
| 46 | 4 | 4 |   | 1 | 0 | 3 | 4 | 4 |
| 51 | 4 | 4 |   | 4 | 1 | 4 | 4 | 4 |
| 52 | 4 | 4 |   | 0 | 3 | 2 | 4 | 4 |
| 53 | 4 | 4 |   | 4 | 2 | 3 | 4 | 4 |
| 54 | 4 | 4 |   | 3 | 2 | 2 | 4 | 4 |
| 55 | 4 | 4 |   | 4 | 2 | 4 | 4 | 4 |
| 56 |   |   |   |   |   |   |   |   |
| 57 | 3 | 4 |   | 0 | 0 | 0 | 0 | 0 |
| 58 | 4 | 4 |   | 0 | 0 | 0 | 3 | 3 |
| 59 | 3 | 4 |   | 1 | 0 | 0 | 3 | 3 |
| 60 | 4 | 4 |   | 0 | 0 | 2 | 4 | 4 |
| 62 | 4 | 4 |   | 0 | 0 | 3 | 4 | 4 |
| 123 | 4 | 3 | 4 | 1 | 0 |   | 4 | 4 |
| 129 | 4 | 4 |   | 0 | 0 | 4 | 4 | 4 |
| 130 | 4 | 4 |   | 1 | 0 | 3 | 4 | 4 |

EXAMPLE 8

This Example illustrates the plant growth regulating properties of the compounds. The compounds were applied in the form of a 4000 ppm solution in distilled water and the solution was then applied to the foliage of young seedlings of various plants. The experiments were replicated twice. After 12 or 13 days from treatment the plants were assessed for plant growth regulating effects and phytotoxic symptoms.

Table III shows the stunting effect of the compounds on the vegetative growth using the following grading:
1=0–30% retardation
2=31–75% retardation
3=75% retardation If no figure is given, the compound was substantially inactive as a stunting agent. Additional plant growth regulating properties are indicated as follows:
G=darker green leaf colour
A=apical effect
T=tillering effect.

TABLE III

| COMPOUND NUMBER | SOYA | COTTON | SUGAR BEET | AGROSTIS TENIUS | CYNODON DACTYLON | DACTYLIS GLOMERATA | WHEAT | BARLEY | MAIZE | TOMATO |
|---|---|---|---|---|---|---|---|---|---|---|
| 1 |   |   | 3G | 2G |   |   | 1 |   |   | G |
| 2 | 1 |   | 2G | 2G | 1 | 1 |   |   | 2 | 1G |
| 6 | 1 |   | 3G | 3 | 2G | 2G | 1G |   |   | 3G |
| 9 | 2G | G | 1 | 1G | 1G | 1G |   | 1T |   | 2G |
| 11 | 2G | 1G | 3G | 3G | 3G | 3G |   |   |   | 3G |
| 12 | 1 |   | 3G | 2G | 1G | 1 | 2 | T |   | 3G |
| 13 | 1G | 2 | 1G |   |   |   | 1GT |   | 2 | 2 |
| 14 | 1G |   | 2G | 1G | 1G | 1G | 1 |   | 2 | 3G |
| 15 | 2G |   | 3G | 1 | 2 | 1 |   |   | 1 | 2GA |
| 17 | G | 2 | 2G |   |   |   |   |   |   | G |
| 18 |   |   | 3 | 2G | 2G | 1 | 1 | 1 | 2 | 3G |
| 19 | 2G | 2 | 2GT | 2 | 1 |   | 1 |   |   | 3GA |
| 20 | 2G | 2G | 2G | 2 | 2 | 2 |   | 1 | 1 | 3GA |
| 21 | 2G | 2G | 2G | 2G | 2G | 2G | 1 | 1 | 1 | 3A |
| 23 | 1 | 2 | 1G | 1 | 1 | 1 |   |   |   | 2GA |
| 25 | 2G | 3G | 3GA | 1 | 1 |   | T |   | 3 | 2G |
| 26 | G | 2G | 1G |   |   |   |   |   | 3 | 3 |

TABLE III-continued

| COMPOUND NUMBER | SOYA | COTTON | SUGAR BEET | AGROSTIS TENIUS | CYNODON DACTYLON | DACTYLIS GLOMERATA | WHEAT | BARLEY | MAIZE | TOMATO |
|---|---|---|---|---|---|---|---|---|---|---|
| 27 | 1G | | 2G | | | | | | 1 | 3G |
| 28 | | | 2G | | | | | | 1 | 2G |
| 31 | 3GA | 2G | 1G | | | | T | 1 | 3 | 3G |
| 32 | 2G | 2 | 3G | 3G | 1 | | 1 | 1 | 1 | 3GA |
| 34 | 2GA | 1G | 2G | 2G | 2G | 2G | | | 3 | 3GA |
| 35 | 2G | 2G | 3GA | 3G | 3G | 2G | 1 | 1 | 2 | 3G |
| 44 | 1GA | G | 3G | | 1G | | T | | 1 | 3GA |
| 46 | 2GT | G | 2G | | | | 1T | | | 2GAT |
| 52 | | | 1 | | | | | T | 1 | |
| 53 | | 1G | 3G | | | | | T | 1 | 2G |
| 54 | G | 1G | 2G | | | | | T | 2 | 3G |
| 55 | 1G | 3G | 3G | | | | 1 | | 1 | 3A |
| 128 | 2G | 2G | 2G | 2G | 2G | 1G | | | | 3GA |
| 129 | 3G | 2G | 2GAT | 3G | 3G | 2G | 1T | | 1 | 3G |

We claim:
1. A method of preventing fungal attack on wood, hides, leather and paint films which comprises applying thereto an effective amount of a compound of formula (I)

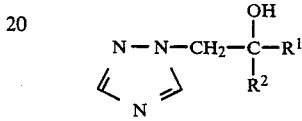

wherein $R^1$ is $C_{1-5}$ alkyl, or halophenyl, and $R^2$ is halophenyl or halobenzyl.

* * * * *